United States Patent [19]

Vennett

[11] 4,056,446
[45] Nov. 1, 1977

[54] DIVERLESS CATHODIC PROTECTION DATA ACQUISITION

[75] Inventor: Richard M. Vennett, Ponca City, Okla.

[73] Assignee: Continental Oil Company, Ponca City, Okla.

[21] Appl. No.: 756,571

[22] Filed: Jan. 3, 1977

[51] Int. Cl.² ............ G01N 27/30; C23F 13/00
[52] U.S. Cl. ................ 204/1 T; 204/147; 204/148; 204/195 C; 204/196; 204/197
[58] Field of Search ......... 204/1 C, 147, 148, 195 C, 204/196, 197; 324/65 CR

[56] References Cited

U.S. PATENT DOCUMENTS

| | | | |
|---|---|---|---|
| 3,071,531 | 1/1963 | Hosford, Jr. | 204/196 |
| 3,649,492 | 3/1972 | Marsh et al. | 204/148 |
| 3,855,102 | 12/1974 | Palmer | 204/196 |
| 3,954,591 | 5/1976 | Conkling | 204/196 |

FOREIGN PATENT DOCUMENTS 1,389,123  4/1975  United Kingdom ............ 204/196

OTHER PUBLICATIONS

D. R. Anthony, "Unique Methods for Applying & Monitoring Platform Cathodic Protection in Cook Inlet, Alaska," *Materials Performance*, Aug. 1974, pp. 9–16.

J. A. Burgbacher, *Materials Protection*, Apr. 1968, pp. 26–30.

*Primary Examiner*—John H. Mack
*Assistant Examiner*—Aaron Weisstuch
*Attorney, Agent, or Firm*—A. Joe Reinert

[57] ABSTRACT

Diverless monitoring of cathodic protection of offshore platforms wherein a reference electrode is passed along a guideline in proximity to a portion of the platform subject to corrosion is improved by maintaining the electrode at a fixed distance and radial direction from the taut guideline, as by slideably mounting a fixed distance from a second parallel taut guideline.

12 Claims, 4 Drawing Figures

DIVERLESS CATHODIC PROTECTION DATA ACQUISITION

BACKGROUND OF THE INVENTION

The invention relates to the diverless acquisition of data useful for determining the extent of cathodic protection of a portion of a structure immersed in salt-containing water and subject to corrosion, in particular, an offshore drilling or production platform. In one aspect, the invention relates to an improvement in a process for obtaining such data. In another aspect, the invention relates to an apparatus for the improved acquisition of such data. In a more particular aspect, the invention relates to improvements in apparatus and process for the obtaining of profiles of electrode potential versus depth in proximity with a portion of such structure under the surface of the sea and susceptible to corrosion. Such data are useful to determine the degree of protection afforded the structure by anodes affixed thereto, the necessity for attachment of additional anodes, the longevity of cathodic protection, and the like, all according to conventional engineering practice known to those skilled in the art.

BRIEF DESCRIPTION OF PRIOR ART

Structures immersed in salt-containing water are subject to considerable attack by salt water corrosion. Extremely important examples of such structures are offshore drilling and production platforms.

Cathodic protection is the primary method of preventing corrosion of the submerged portions of such offshore structures. For example, one system, utilizing lead-silver-antimony anodes calls for placing a number of small anodes on each platform leg. Other systems utilize large lead-platinum anodes placed on diagonal and horizontal members. Yet other systems are in use.

Periodic inspection and maintenance of such cathodic protection systems is essential to ensure the long term integrity of the structure and the safety of the operating personnel.

Thus, it has been reported that platforms having lead-silver-antimony anode system had partial protection of the legs but little or no protection on the horizontals or diagonals and that with the lead-platinum system, the opposite was true.

The only practical way known at present to ensure that the structure is cathodically protected is to measure its electro-chemical potential with a standard reference cell. Because offshore structures are so large, especially in deep water, the potential can vary significantly over the structure. Some portions, particularly near the bottom, can be freely corroding, while a remote reference cell dipped into the water near the surface records a supposedly protected structure.

Experiences in the Gulf of Mexico in recent years have demonstrated a need for electrode potential profiles of structures as a function of depth. One commonly used technique employs a diver carrying one or more reference cells who descends down a platform leg. He places a hand-held probe in the mud while the potential is measured and recorded on the surface. The diver then begins his ascent. He stops every five-ten feet to place the reference cell against the leg for a potential reading. This technique provides an accurate potential profile along the leg of the structure, but becomes prohibitively expensive for structures in water over 300 feet deep, and is very expensive for even shallower structures.

Diverless monitoring systems have been proposed for the acquisition of data useful in determining cathodic protection for such structures. Thus, D. R. Anthony, *Materials performance,* August, page 9-16 (1974) on page 10 discloses that potential measurements on offshore platforms are made at various depths using a silver-silver chloride (Ag-AgCl) reference electrode suspended from the platform deck. However, it is also disclosed that erroneous potential results were obtained with such free swinging reference electrodes because the water was constantly moving and because the exact location of the electrode was not known.

Hence, as the article discloses, two techniques are currently being used to obtain valid potential readings. One consists of having a diver take a reference electrode below the surface. As has been pointed out before, this is very costly and time consuming. The other process consists of installing temporary weighted guidelines at locations on the structure where protection will be the most difficult to achieve. A reference electrode is then fastened to the guideline in such a way that it can be run up and down the line. Potentials can then be measured at various depths at these fixed locations on the structure.

Though this latter diverless process constitutes a considerable advance in the art, it has been found that improvement is still needed such that the electrode potential data can be correlated with a precise location of the reference electrode with reference to the structure.

This invention constitutes a substantial advance in the art for providing for precise placement of the electrode with reference to points on the structure and also provides a ready means of correlating the electrode potential data with a precise location of the electrode with reference to a locus on the structure. Consequently, data acquired by the process and apparatus of my invention has substantially improved usefulness over that obtained by prior art diverless acquisition methods because the precise depth of the electrode was often not known by the prior methods due to twisting of the line used to raise and lower it about the guideline due to current eddies from the platform structure, because the line often became fouled in the guideline, and because the radial direction of the electrode from the guideline was not known or controllable by such previous methods or apparatus.

OBJECTS OF THE INVENTION

An object of the invention is to provide an improved process for diverless acquisition of data useful for determining cathodic protection of a portion of a structure immersed in salt-containing water and subject to corrosion.

Another object of the invention is to provide apparatus for the diverless acquisition of data useful for determining cathodic protection of a portion of a structure immersed in salt-containing water and subject to corrosion.

SUMMARY OF THE INVENTION

Improvement in a process and apparatus for diverless acquisition of data useful in determining cathodic protection of a portion of a structure immersed in salt-containing water and subject to corrosion wherein the structure extends from contact with the bottom of the body of water to above the surface of the body of water involves passing a reference electrode along a guideline to a definite point along the length of the guideline wherein the guideline is fastened on one end to the structure above the surface and on the other end to an anchoring means near the bottom such that the guideline passes in proximity to the portion of the structure to be sensed for protection, and wherein the electrode is slideably mounted on the guideline, and recovering electrode potential data from the electrode at a definite point of the guideline while maintaining the guideline taut and maintaining the electrode at a fixed distance from the guideline. Apparatus useful to accomplish the result in a presently preferred mode comprises an anchoring means near the bottom, a first taut guideline attached on one end to the anchoring means and attached on the other end to a member of the structure above the surface of the water, a second taut guideline attached to the anchoring means and attached to the member of the structure above the surface such that the second taut guideline is parallel to the first taut guideline and such that both guidelines pass within proximity of the portion of the structure subject to corrosion, a saddle slideably attached to the first guideline and the second guideline, a reference electrode mounted in association with the saddle, a readout attached in electrical communication to the electrode, a line for raising and lowering the electrode and saddle assembly on the guidelines, and a means for determining the depth to which the line is played out and consequently the position of the electrode and saddle assembly.

According to another aspect of the invention, improved means are provided for maintaining tension on the taut guidelines.

BRIEF DESCRIPTION OF THE DRAWINGS

The drawing in FIG. 1 illustrates an offshore platform with the diverless monitoring system installed.

The drawing in FIG. 2 illustrates a side cross view of an upper guideline support for attaching the guidelines to a structure member and having a means for maintaining tension from the top of the guidelines.

Figure 3:
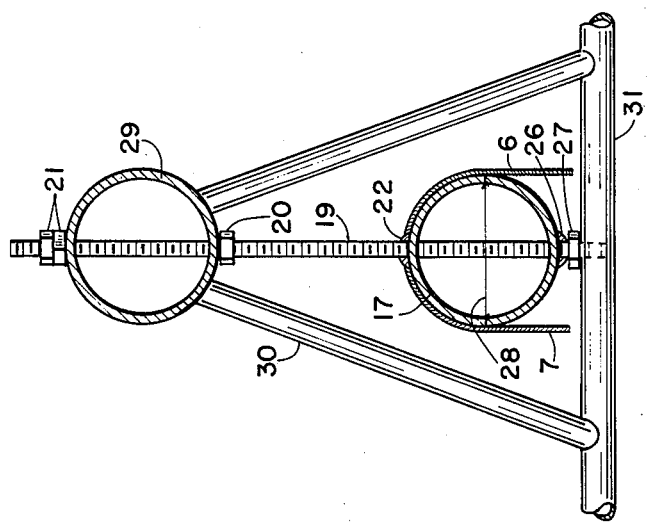
Figure 2:
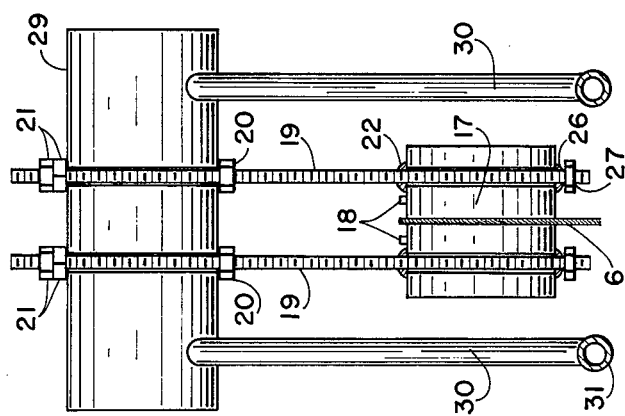

The drawing in FIG. 3 illustrates a front cross view of the device shown in FIG. 2.

Figure 4:
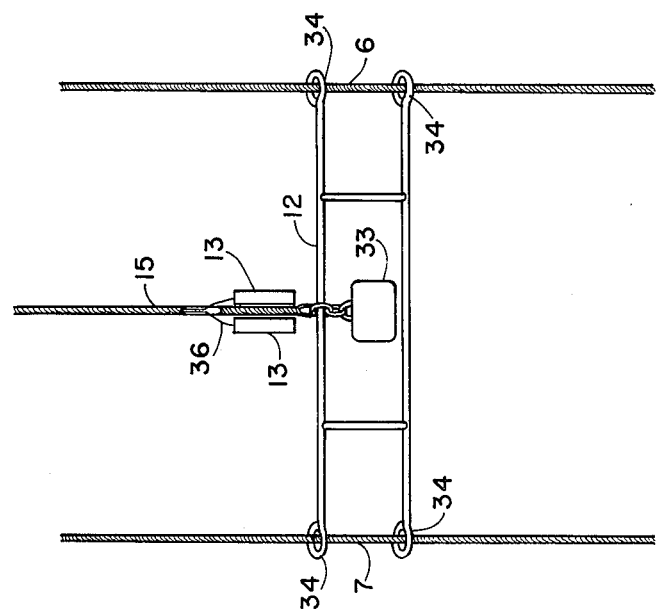

FIG. 4 illustrates a saddle and reference electrode assembly.

DESCRIPTION OF THE DRAWINGS

Figure 1:
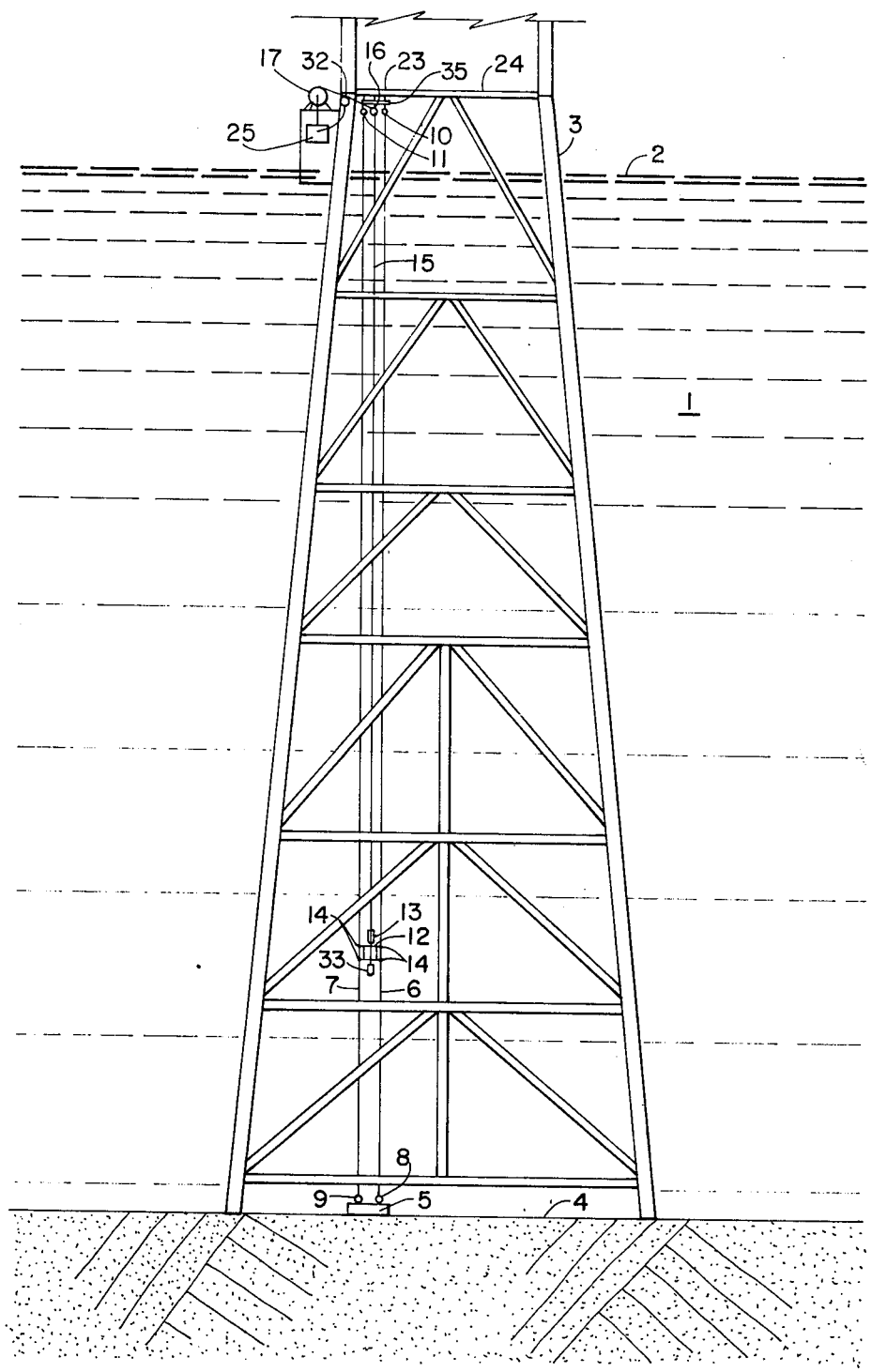

FIG. 1 illustrates a schematic cross section of a structure partially immersed in salt-containing water and having an exemplary apparatus for diverless acquisition of data associated therewith.

The salt-containing water 1 having a surface 2 has a structure 3 such as an offshore production or drilling platform affixed to the bottom 4.

According to a presently preferred mode for existing offshore structures, an anchoring means 5 securely rests on bottom 4 in proximity to the offshore structure 3. Guidelines 6 and 7 are fastened to anchoring means 5 by fasteners 8 and 9 and to cross member 24 of the structure by means of fasteners 10 and 11, mounting bar 35 and tensioning means 23 such that the guidelines are taut, parallel to each other, substantially vertical, and each in a fixed radial direction from the other throughout their lengths. A reference electrode 13 is fixedly mounted in association with a saddle 12 which is slideably attached to the guidelines 6 and 7 by slides 14, and can be raised and lowered along the guidelines in proximity to the structure by means of line 15 attached to the saddle assembly and which passes over pulley 16, measuring capstan 32, to be wound or unwound from cable winch 17. Readout 25 is in electrical communication with reference electrode 13 through an electrically conductive portion of line 15 and is also in communication with capstan 32 to provide a readout of the position of the electrode correlated with electrode potential data. The readout can be any conventional device of this type.

FIG. 2 presents a side view and FIG. 3 presents a front view of a presently preferred mode of attaching the guidelines 6 and 7 on the upper end to the structure and providing for tensioning the guidelines in the proper relationship. Guidelines 6 and 7 are tensioned to tautness by mounting over the cylindrical member 17 having a diameter 28 which is the same as the distance between the attachment points on the anchoring means such that the diameter 28 is in the same horizontal direction as the line between the anchoring points and is horizontally parallel thereto. Projections 18 hold the guidelines in the proper position. Frame members 30 and 31 hold upper tensioning frame 29 in the proper position on the structure. Tensioning bolts 19 are fixed to cylindrical member 17 by welds 22 and 26 and nuts 27. Proper tensioning is effected by means of adjustment of nuts 20 and 21 to obtain the tensioning and positioning of the guidelines as specified above.

FIG. 4 illustrates a cross sectional view of the saddle and electrode assembly. Weight 33 holds line 15 taut to ensure accuracy of positioning as indicated by capstan 32 on FIG. 1. Reference electrodes 13 are mounted in association with the saddle 12 which is slideably attached to guidelines 6 and 7 by slideable mountings 34. The weight 33 must be sufficient to maintain line 15 taut at all times. Line 15 contains an inner insulated electrical conductor 36 providing electrical communication between reference electrode 13 and readout 25 and being otherwise electrically insulated. Guidelines 34 are electrically insulated from the structure and from the saddle and electrode assembly by means of electrical insulation, preferably a plastic coating.

PREFERRED EMBODIMENTS

The saddle assembly, weight, and the like are insulated from the reference electrode, preferably with a plastic coating.

According to one presently preferred embodiment, both $Cu/CuSO_4$ and $Ag/AgCl$ electrodes are mounted in association with the saddle and connected to readouts to provide redundency in the system and to provide improved data acquisition for determining cathodic protection.

According to a presently preferred embodiment, particularly where a new platform is being constructed, the anchoring means near the bottom constitutes a cylindrical member rigidly affixed to the platform, extending in a horizontal direction to provide proper relationship of the guidelines, being of proper diameter to provide for proper distance between the guidelines, and having projections to hold the guidelines in proper position such that one continuous length of guideline can be looped under the member to provide the guidelines and such that the guidelines can be replaced upon deterioration by simply tying a new guideline to the old and pulling under the member until emplaced.

The slidable mountings 34 are according to a presently preferred embodiment of a snap-ring design such that the saddle can be easily detached from the guidelines between data surveys.

The process and apparatus of this invention lead to acquisition of data of greatly improved value because the depth of the electrode is readily determined since the electrode and line does not twist about the guideline, as has been determined to be a problem with prior systems and devices. The problem of fouling of the line about the guideline which occurs under many current conditions is also eliminated. Also, the electrode is maintained in a fixed relationship with the guideline.

EXAMPLES

To illustrate the invention, an offshore platform is rigged with a diverless data acquisition system as illustrated as in FIG. 1. The reference electrode is passed from the anchor to near the surface of the water and recordings are made of electrochemical potential versus depth as recorded by the capstan contacting the line pulling the electrode and assembly to the surface such that electrode potentials are presented versus depth on the readout.

From these data it is determined that certain locations on the structure are not sufficiently protected by cathodic protection and anodes are placed in electrical communication to the structure in proximity to such points.

The scans are repeated in the above manner at six month intervals to ensure that the cathodic protection on the structure is adequate and that the protection has not deteriorated.

These examples are provided in order to more fully explain the present invention and provide information to those skilled in the art sufficient to carry it out. However, it is to be understood that these examples are not intended to function as limitations on the invention as described and claimed herein.

I claim:

1. In a process for diverless acquisition of data useful for determining cathodic protection of a portion of a structure immersed in salt-containing water and subject to corrosion wherein the structure extends from contact with the bottom of the body of water to above the surface of the body of water and wherein the process comprises:
    a. passing a reference electrode along a guide line to a definite point along the length of the guideline wherein the guideline is fastened on one end to the structure above the surface and on the other end to an anchoring means near the bottom such that the guideline passes in proximity to the portion of the structure to be sensed for protection, wherein the electrode is slideably mounted on the guideline, and
    b. recovering electrode potential data from the electrode at the definite point on the guideline; the improvement comprising:
    c. maintaining the guideline taut and maintaining the electrode at a fixed distance from the guideline and in a fixed radial direction from the guideline.

2. The process of claim 1 wherein the electrode is maintained at the fixed distance and in the fixed radial direction from the taut guideline by slideably mounting same at a fixed distance and in a fixed radial direction from a second taut guideline which runs parallel to the guideline of claim 1.

3. The process of claim 2 wherein the data is acquired at a series of points along the length of the guidelines and at a fixed radial direction and distance from the taut guidelines.

4. The process of claim 3 wherein continuous data is acquired from a large number of points traversed by the electrode over a substantial distance along the guidelines and wherein multiple scans for the acquisition of data are conducted over a period of time.

5. The process of claim 2 wherein the electrode is mounted in a saddle which is slideably mounted on the taut guidelines, wherein the saddle and the electrode are weighted sufficiently to move downward along the guidelines on their own accord, wherein the electrode is electrically connected to a readout on the structure, wherein the electrode and saddle assembly is raised and lowered by means of a line from the structure, wherein the vertical position of the assembly is determined by the amount of line playted out, wherein the line and the guidelines are electrically insulated from the structure.

6. The process of claim 5 wherein data is acquired at a series of points along the guideline to obtain an electrode potential profile over a substantial amount of the distance near a portion of the structure subject to corrosion.

7. The process of claim 6 wherein a continuous series of points is obtained and multiple scans are made at different points in time.

8. The process of claim 6 wherein the guidelines are substantially vertical wherein the depth of the electrode is determined by a capstan measurement of the length of line played out, and wherein the depth of electrode and the electrode potential data are simultaneously presented by the readout.

9. An apparatus for diverless acquisition of data useful for determining cathodic protection of a portion of a structure immersed in salt-containing water and subject to corrosion wherein the structure extends from contact with the bottom of the body of water to above the surface of the body of water comprising in combination with said partially immersed structure:
    (a). an anchoring means near the bottom,
    (b). a first taut guideline contacting the anchoring means on one end and the other end contacting the member of the structure above a surface of the water,
    (c). a second taut guideline contacting the anchoring means and contacting the member of the structure above the surface such that the second taut guideline is parallel to the first taut guideline and such that both guidelines pass within proximity of the portion of the structure subject to corrosion,
    (d). a saddle slideably attached to the first guideline and the second guideline,
    (e). a reference electrode mounted in association with the saddle such that its radial direction and distance from the first guideline remains constant,
    (f). a readout attached in electrical communication to the electrode,
    (g). a line for raising and lowering the electrode and the saddle assembly on the guidelines attached on one end to the electrode and saddle assembly, and
    (h). means for determining the depth to which the line is played out and consequently the position of the electrode and saddle assembly.

10. The apparatus of claim 9 wherein a tensioning means is provided for attaching the first guideline and the second guideline to the member of the structure and for tensioning the guidelines to tautness.

11. The apparatus of claim 10 wherein the tensioning means comprises a cylindrical member having a diameter equal to the distance between the guidelines, frame members mounted on the member of the structure to support a tensioning frame, and tensioning bolts attached to the cylindrical member and passing through the tensioning frame and having nuts for tensioning the guidelines passed over the cylindrical member to tautness.

12. The apparatus of claim 10 wherein the guidelines are substantially vertical, wherein a winch is attached to the end of the line opposite the electrode and saddle assembly for raising and lowering the saddle assembly along the guidelines, wherein the electrode and saddle assembly are sufficiently weighted to provide tension on the line, wherein the line contains an insulated electrical conductor for conducting electrical data from the electrode to the readout, wherein the line and guidelines are electrically insulated from the structure, and wherein the means for determining the depth to which the line is played out and consequently the position of the electrode and saddle assembly comprises a capstan driven by passage of the line which is in data communication with the readout.

* * * * *